US012344596B2

(12) United States Patent
Li et al.

(10) Patent No.: US 12,344,596 B2
(45) Date of Patent: Jul. 1, 2025

(54) SOLID FORMS OF (S)-1-((2',6-BIS(DIFLUOROMETHYL)-[2,4'-BIPYRIDIN]-5-YL)OXY)-2,4-DIMETHYLPENTAN-2-AMINE AND SALTS THEREOF

(71) Applicant: Lexicon Pharmaceuticals, Inc., The Woodlands, TX (US)

(72) Inventors: Qun Li, Newark, DE (US); Wenxue Wu, Princeton Junction, NJ (US); Matthew Mangzhu Zhao, Edison, NJ (US)

(73) Assignee: LEXICON PHARMACEUTICALS, INC., The Woodlands, TX (US)

( * ) Notice: Subject to any disclaimer, the term of this patent is extended or adjusted under 35 U.S.C. 154(b) by 219 days.

(21) Appl. No.: 18/114,104

(22) Filed: Feb. 24, 2023

(65) Prior Publication Data

US 2023/0357182 A1 Nov. 9, 2023

Related U.S. Application Data

(60) Provisional application No. 63/315,507, filed on Mar. 1, 2022.

(51) Int. Cl.
| | |
|---|---|
| *A61P 25/04* | (2006.01) |
| *A61K 9/28* | (2006.01) |
| *A61K 31/444* | (2006.01) |
| *A61P 29/00* | (2006.01) |
| *C07D 213/65* | (2006.01) |
| *C07D 401/04* | (2006.01) |

(52) U.S. Cl.
CPC .............. *C07D 401/04* (2013.01); *A61K 9/28* (2013.01); *A61K 31/444* (2013.01); *A61P 29/00* (2018.01); *C07B 2200/13* (2013.01)

(58) Field of Classification Search
None
See application file for complete search history.

(56) References Cited

U.S. PATENT DOCUMENTS

| | | | |
|---|---|---|---|
| 9,902,722 B2 * | 2/2018 | Luo | ....................... C07D 239/26 |
| 2018/0346440 A1 | 12/2018 | Bronson et al. | |
| 2024/0343720 A1 | 10/2024 | Li et al. | |

FOREIGN PATENT DOCUMENTS

| | | |
|---|---|---|
| WO | 2017059085 A1 | 4/2017 |
| WO | 2021216441 A1 | 10/2021 |
| WO | 2023051749 A1 | 4/2023 |

OTHER PUBLICATIONS

Luo et al. "Discovery of (S)-1-((2',6-Bis(difluoromethyl)-[2,4'-bipyridin]-5-yl)oxy)-2,4-dimethylpentan-2-amine (BMS-986176/LX-9211): A Highly Selective, CNS Penetrable, and Orally Active Adaptor Protein-2 Associated Kinase 1 Inhibitor in Clinical Trials for the Treatment of Neuropathic Pain" Mar. 8, 2022.*
U.S. Appl. No. 18/114,050.
Bastin, Richard J, et al., "Salt Selection and Optimisation Procedures for Pharmaceutical New Chemical Entities", Organic Process Research & Development 4, 427-435 (2000).
Boge, M , et al., "A Membrane-proximal Tyrosine-based Signal Mediates Internalization of the HIV-1 Envelope Glycoprotein via Interaction with the AP-2 Clathrin Adaptor", J Biol Chem 273, 15773-15778 (1998).
Buonanno, A , "The Neuregulin Signaling Pathway and Schizophrenia: From Genes to Synapses and Neural Circuits", Brain Res Bull 83, 122-131 (2010).
Caira, M. , et al., "Crystalline Polymorphism of Organic Compounds", Topics in Current Chemistry, vol. 198, 163-208 (1998).
Conner, S , et al., "AAK1-Mediated m2 Phosphorylation is Stimulated by Assembled Clathrin", Traffic 4, 885-890 (2003).
Conner, S , et al., "Skip Nav Destination Article| Mar. 4, 2002 Identification of an adaptor-associated kinase, AAK1, as a regulator of clathrin-mediated endocytosis", J Cell Bio 156, 921-929 (2002).
Greenwood, T , et al., "Analysis of 94 candidate genes and 12 endophenotypes for schizophrenia from the Consortium on the Genetics of Schizophrenia", Am J Psychiatry 168, 930-946 (2011).
Hartz, R , et al., "Discovery, Structure-Activity Relationships, and In Vivo Evaluation of Novel Aryl Amides as Brain Penetrant Adaptor Protein 2-Associated Kinase 1 (AAK1) Inhibitors for the Treatment of Neuropathic Pain", J Med Chem 64 (15), 11090-11128 (2021).
Henderson , et al., "A Novel AAK1 Splice Variant Functions at Multiple Steps of the Endocytic Pathway", Mol Biol Cell 18, 2698-2706 (2007).
Hilfiker, R , "Polymorphism in the Pharmaceutical Industry", ISBN: 978-4-637-42257-0, pp. 1-19 (2006).
Jaaro-Peled, H , et al., "Review of Pathological Hallmarks of Schizophrenia: Comparison of Genetic Models With Patients and Nongenetic Models", Schizophrenia Bulletin 36, 301-313 (2010).
Kuai, L , et al., "AAK1 Identified as an Inhibitor of Neuregulin-1/ErbB4-Dependent Neurotrophic Factor Signaling Using Integrative Chemical Genomics and Proteomics", Chemistry and Biology 18, 891-906 (2011).
Latourelle, J , et al., "Genomewide association study for onset age in Parkinson disease", BMC Med Genet 10, 98, doi: 10.1186/1471-2350-10-98 (2009).
Motely, A , et al., "Functional Analysis of AP-2 α and μ2 Subunits", Mol Biol Cell 17, 5298-5308 (2006).
Neveu, G , et al., "AP-2-associated protein kinase 1 and cyclin G-associated kinase regulate hepatitis C virus entry and are potential drug targets", J Virol 89 (8), 4387-4404 (2015).
Neveu, G , et al., "Identification and Targeting of an Interaction between a Tyrosine Motif within Hepatitis C Virus Core Protein and AP2M1 Essential for Viral Assembly", PLoS Pathog 8, 1-16, e1002845.doi:10.1371/journal.opat.1002845 (2012).

(Continued)

*Primary Examiner* — Kortney L. Klinkel
*Assistant Examiner* — Alison Azar Salamatian
(74) *Attorney, Agent, or Firm* — Viksnins Harris Padys Malen LLP

(57) ABSTRACT

Salts of the AAK1 inhibitor (S)-1-((2',6-bis(difluoromethyl)-[2,4'-bipyridin]-5-yl)oxy)-2,4-dimethylpentan-2-amine and solid forms thereof are disclosed, as are pharmaceutical formulations comprising them and methods of their preparation.

11 Claims, 3 Drawing Sheets

(56) References Cited

OTHER PUBLICATIONS

Figure 1:
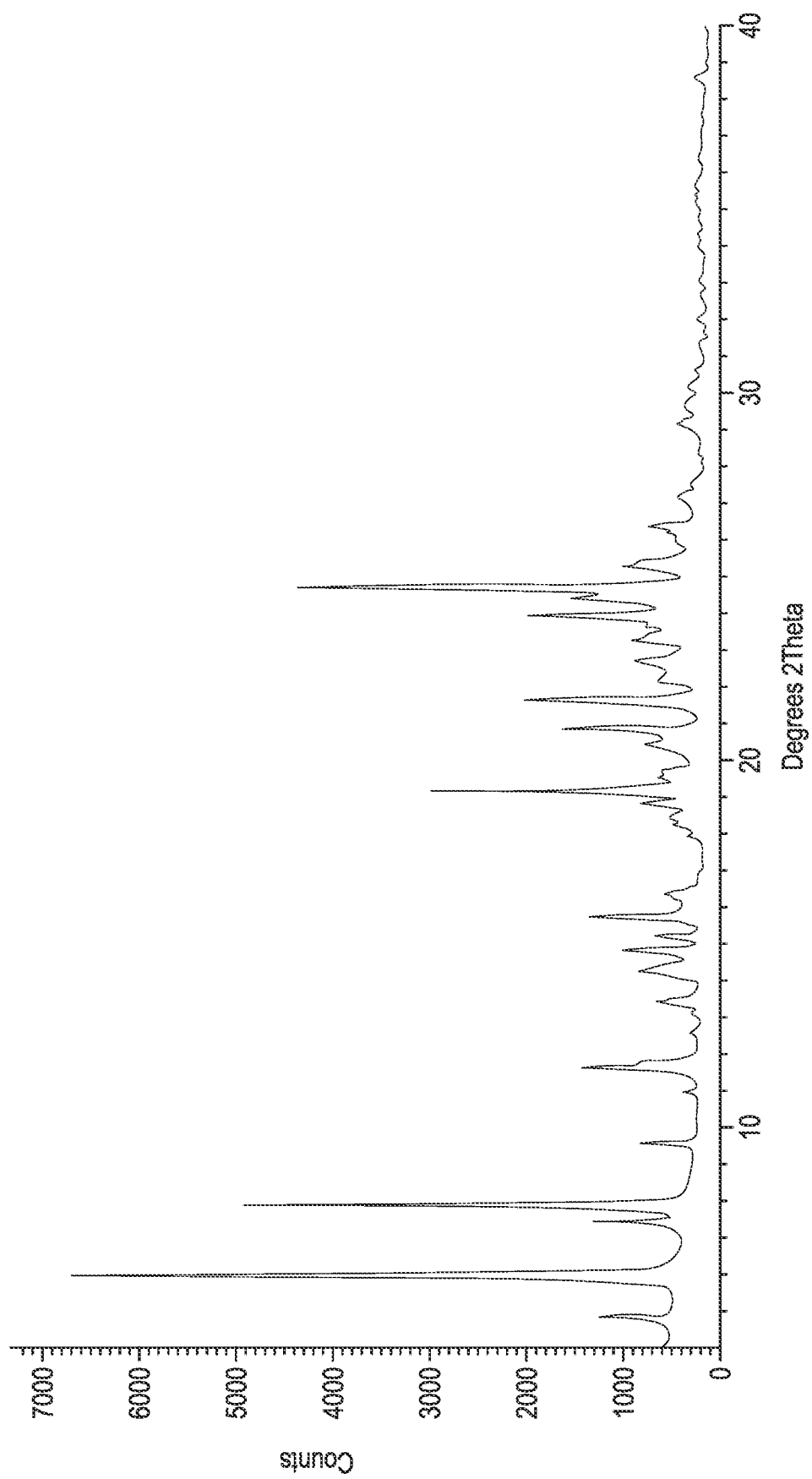

Patent Cooperation Treaty, International Search Report and Written Opinion for PCT/US2023/013851, 11 pages dated May 17, 2023.
Ricotta, D, et al., "Phosphorylation of the AP2μ subunit by AAK1 mediates high affinity binding to membrane protein sorting signals", J Cell Bio 156, 791-795 (2002).
Thackaberry, E, "Non-clinical toxicological considerations for pharmaceutical salt selection", Expert Opinion on Drug Metabolism & Toxicology 8(11), 1419-1433 (2012).
Wen, L, et al., "Neuregulin 1 regulates pyramidal neuron activity via ErbB4 in parvalbumin-positive interneurons", Proc Natl Acad Sci 107, 1211-1216 (2010).

* cited by examiner

SOLID FORMS OF (S)-1-((2',6-BIS(DIFLUOROMETHYL)-[2,4'-BIPYRIDIN]-5-YL)OXY)-2,4-DIMETHYLPENTAN-2-AMINE AND SALTS THEREOF

1 FIELD OF THE INVENTION

This application relates to solid forms of (S)-1-((2',6-bis(difluoromethyl)-[2,4'-bipyridin]-5-yl)oxy)-2,4-dimethyl-pentan-2-amine, pharmaceutically acceptable salts thereof, compositions comprising them and methods of their use.

2 BACKGROUND OF THE INVENTION

Adaptor associated kinase 1 (AAK1) is a member of the Ark1/Prk1 family of serine/threonine kinases. AAK1 mRNA exists in two splice forms termed short and long. The long form predominates and is highly expressed in brain and heart (Henderson and Conner, *Mol. Biol. Cell.* 2007, 18, 2698-2706). AAK1 is enriched in synaptosomal preparations and is co-localized with endocytic structures in cultured cells. AAK1 modulates clathrin coated endocytosis, a process that is important in synaptic vesicle recycling and receptor-mediated endocytosis. AAK1 associates with the AP2 complex, which links receptor cargo to the clathrin coat. The binding of clathrin to AAK1 stimulates AAK1 kinase activity (Conner et al., *Traffic* 2003, 4, 885-890; Jackson et al., *J. Cell. Biol.* 2003, 163, 231-236). AAK1 phosphorylates the mu-2 subunit of AP-2, which promotes the binding of mu-2 to tyrosine containing sorting motifs on cargo receptors (Ricotta et al., *J. Cell Bio.* 2002, 156, 791-795; Conner and Schmid, *J. Cell Bio.* 2002, 156, 921-929). Mu2 phosphorylation is not required for receptor uptake, but phosphorylation enhances the efficiency of internalization (Motely et al., *Mol. Biol. Cell.* 2006, 17, 5298-5308).

AAK1 has been identified as an inhibitor of Neuregulin-1/ErbB4 signaling in PC12 cells. Loss of AAK1 expression through RNA interference mediated gene silencing or treatment with the kinase inhibitor K252a (which inhibits AAK1 kinase activity) results in the potentiation of Neuregulin-1 induced neurite outgrowth. These treatments result in increased expression of ErbB4 and accumulation of ErbB4 in or near the plasma membrane (Kuai et al., *Chemistry and Biology* 2011, 18, 891-906). NRG1 and ErbB4 are putative schizophrenia susceptibility genes (Buonanno, *Brain Res. Bull.* 2010, 83, 122-131). SNPs in both genes have been associated with multiple schizophrenia endophenotypes (Greenwood et al., *Am. J. Psychiatry* 2011, 168, 930-946). Neuregulin 1 and ErbB4 KO mouse models have shown schizophrenia relevant morphological changes and behavioral phenotypes (Jaaro-Peled et al., *Schizophrenia Bulletin* 2010, 36, 301-313; Wen et al., *Proc. Natl. Acad. Sci. USA.* 2010, 107, 1211-1216). In addition, a single nucleotide polymorphism in an intron of the AAK1 gene has been associated with the age of onset of Parkinson's disease (Latourelle et al., *BMC Med. Genet.* 2009, 10, 98). These results suggest that inhibition of AAK1 activity may have utility in the treatment of schizophrenia, cognitive deficits in schizophrenia, Parkinson's disease, neuropathic pain, bipolar disorder, and Alzheimer's disease.

In addition, studies using Huh-7.5 cells indicate a potential utility for AAK1 kinase inhibitors in the treatment of hepatitis C (HCV) infection. Reduction of AAK1 protein using RNA interference mediated gene silencing, treatment with the kinase inhibitor sunitinib (a potent AAK1 inhibitor), and overexpression of Mu2 (AAK1 substrate) phosphorylation site mutant all result in reduced HCV virion assembly. Furthermore, the same treatments were shown to inhibit HCV entry, suggesting AAK1 inhibitors can disrupt two host dependent stages of the virus life cycle (Neveu et al., *PLoS Pathog.* 2012, 8, 1-16; Neveu et al., *J. Virol.* 2015, posted online 4 February). AAK1 inhibitors may also be useful against HIV and HBV (See, e.g., Boge et al., *J. Biol. Chem.* 1998, 273, 15773-15778).

A number of AAK1 inhibitors have disclosed in the literature. See, e.g., Hartz, R. A., et al., *J. Med. Chem.*, 2021 Aug. 12; 64(15):11090-11128. One example is the specific AAK1 inhibitor (S)-1-((2',6-bis(difluoromethyl)-[2,4'-bipyridin]-5-yl)oxy)-2,4-dimethylpentan-2-amine, which has been prepared on a small, laboratory scale. See, e.g., U.S. Pat. No. 9,902,722. Unfortunately, synthetic approaches useful in the laboratory setting are rarely suitable for large-scale manufacture of pharmaceutically acceptable material. For example, the creation of potentially harmful reaction byproducts needs to be minimized, and the use of toxic solvents and reagents are preferably avoided. Moreover, reaction conditions that may work on a gram scale are often inefficient or even dangerous when scaled up.

Similarly, solid forms of a compound that may be sufficient for pre-clinical testing (e.g., amorphous forms), are not necessarily suitable for large scale manufacture and storage. Some forms may be more stable than others. For example, some forms may decompose more readily when exposed to heat or moisture; others may change to forms having different pharmacological properties (e.g., bioavailability) than the original. Some may have solubility profiles that render formulation difficult; others may be more difficult to obtain without impurities that could affect their safety when administered to patients. Consequently, a need exists for solid forms of (S)-1-((2',6-bis(difluoromethyl)-[2,4'-bipyridin]-5-yl)oxy)-2,4-dimethylpentan-2-amine, or pharmaceutically acceptable salts thereof, that can be prepared in commercially useful quantities, are stable, and are readily formulated into safe and effective dosage forms.

3 SUMMARY OF THE INVENTION

This application is directed to solid forms of the adaptor associated kinase 1 (AAK1) inhibitor (S)-1-((2',6-bis(difluoromethyl)-[2,4'-bipyridin]-5-yl)oxy)-2,4-dimethylpentan-2-amine (Compound J) and salts thereof.

A particular embodiment of this invention encompasses solid forms of ((S)-1-((2',6-bis(difluoromethyl)-[2,4'-bipyridin]-5-yl)oxy)-2,4-dimethylpentan-2-aminium dihydrogen phosphate (Compound K):

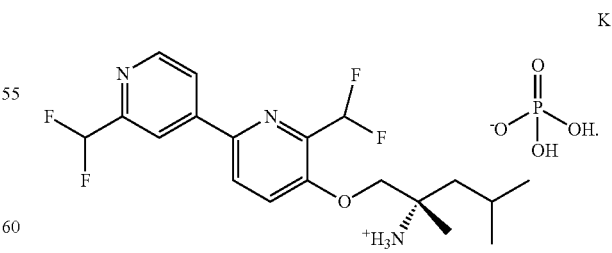

Other embodiments of the invention encompass methods of preparing Compound K and pharmaceutical compositions comprising it. This invention also encompasses methods of its use to treat or manage diseases and disorders, including pain (e.g., neuropathic pain) and viral infections.

4 BRIEF DESCRIPTION OF THE DRAWINGS

FIG. 1 provides a representative X-ray powder diffraction (XRPD) pattern of crystalline solid form I of ((S)-1-((2',6-bis(difluoromethyl)-[2,4'-bipyridin]-5-yl)oxy)-2,4-dimethylpentan-2-aminium dihydrogen phosphate (Compound K). The spectrum was obtained using a Bruker X-ray diffractometer with a LYNXEYE detector (copper Kα radiation).

Figure 2:
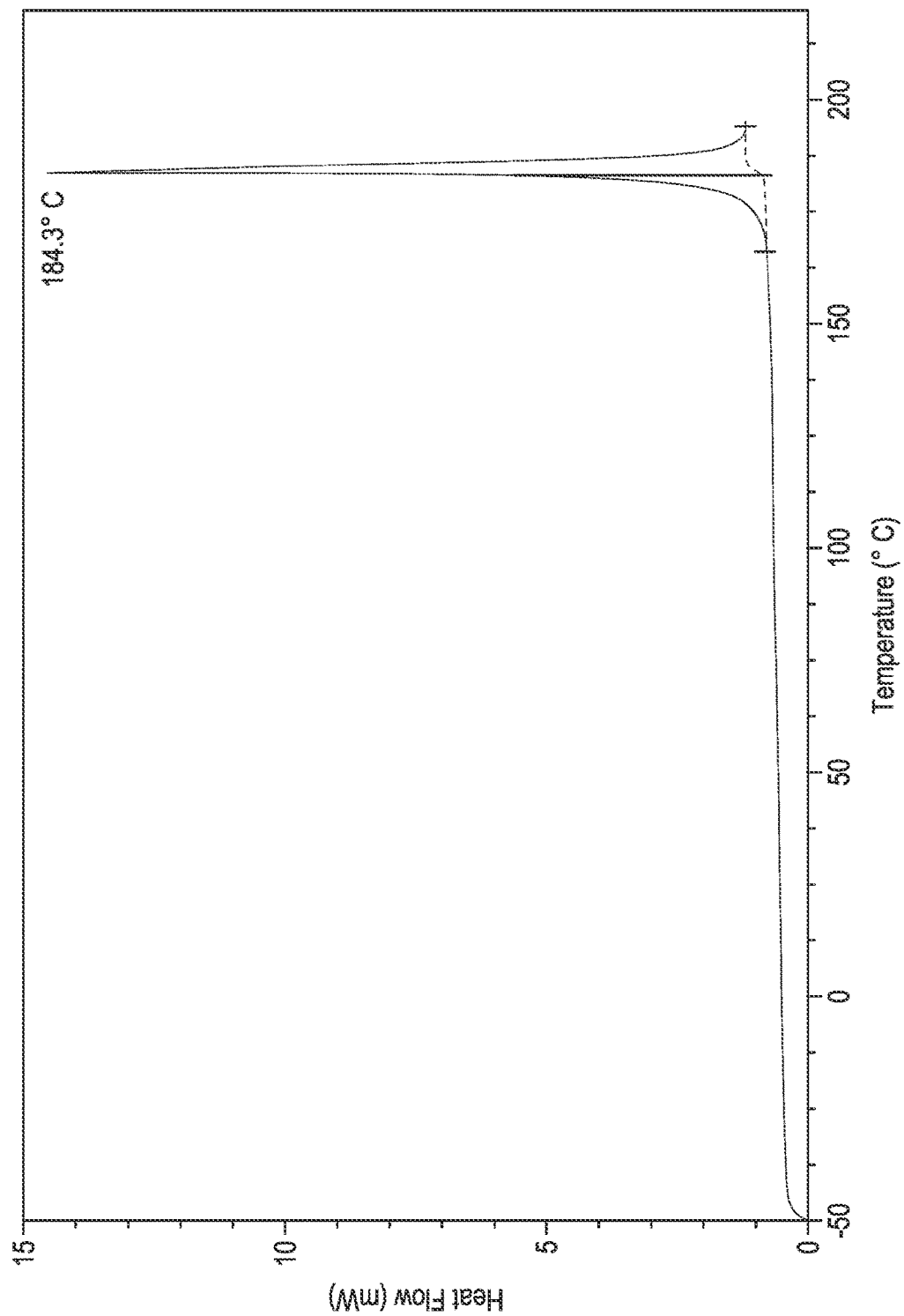

FIG. 2 provides a representative differential scanning calorimetry (DSC) thermogram of a crystalline solid form of Compound K. The thermogram was obtained using a TA Instruments DSC Q2000 instrument and a hermetically sealed gold crucible filled under ambient conditions. Two scans were performed. After the melting was completed in the first scan, the sample was rapidly cooled at approximately −40 K per minute to −50° C., and a second scan was recorded. The heating rate was 10 K per minute in both scans.

Figure 3:
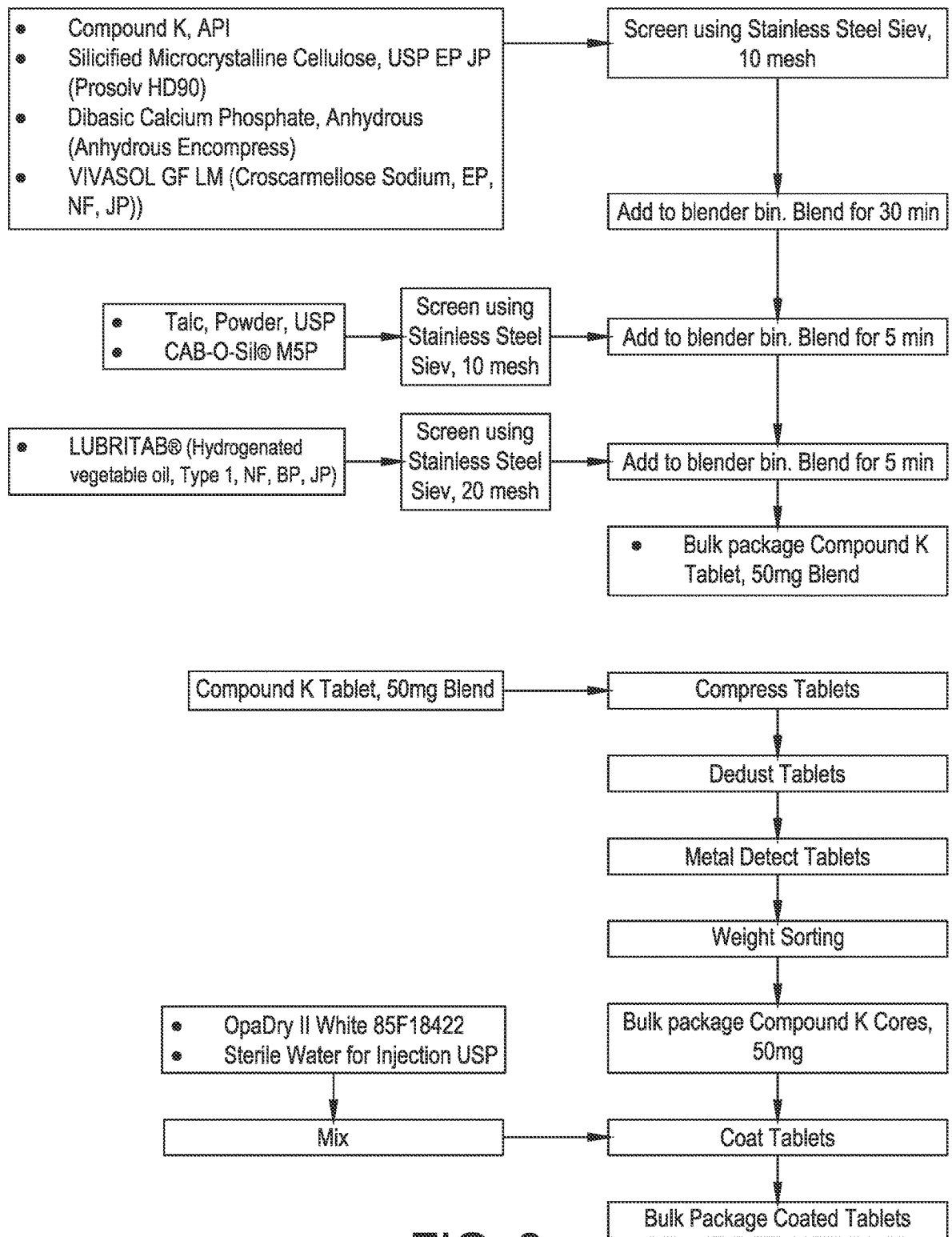

FIG. 3 provides a flowchart of the process used to prepare tablets comprising 50 mg of Compound K.

5 DETAILED DESCRIPTION

This invention is directed to (S)-1-((2',6-bis(difluoromethyl)-[2,4'-bipyridin]-5-yl)oxy)-2,4-dimethylpentan-2-amine (Compound J):

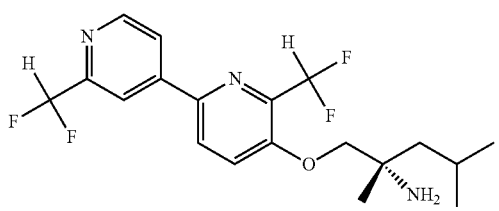

J and pharmaceutically acceptable salts thereof. Particular salts include hydrochloride and phosphate salts.

5.1 Definitions

Unless otherwise indicated, the phrases "compounds of the invention," "compounds of the present disclosure," and the like refer to the compounds disclosed herein.

Unless otherwise indicated, the term "include" has the same meaning as "include, but are not limited to," and the term "includes" has the same meaning as "includes but is not limited to." Similarly, the term "such as" has the same meaning as the term "such as, but not limited to."

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder or changing the way that a patient responds to the disease or disorder.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, that provides a therapeutic benefit in the treatment or management of the disease or condition. The term "therapeutically effective amount" can encompass an amount that improves overall therapy, reduces, or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

5.2 Salts and Solid Forms

This invention is the result of extensive research and experimentation directed at discovering whether thermodynamically and chemically stable pharmaceutically acceptable salts of the AAK1 inhibitor (S)-1-((2',6-bis(difluoromethyl)-[2,4'-bipyridin]-5-yl)oxy)-2,4-dimethylpentan-2-amine (Compound J):

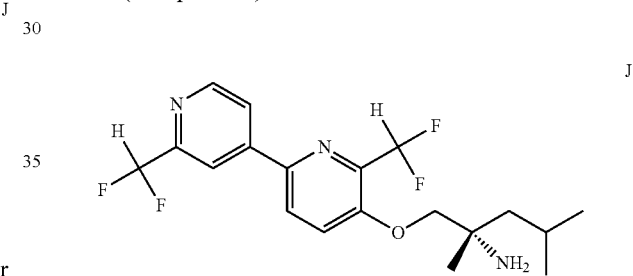

J could be manufactured with high purity on a large, commercial scale. The research was further directed to discovering whether any thermally stable crystalline solid forms of those salts could be repeatedly prepared under such conditions, and whether any of those have suitable physical (e.g., flowability, solubility) properties for use in the manufacture of pharmaceutical dosage forms.

First, a crystalline form of the free base of Compound J was prepared and studied. However, neither it nor any other solid forms of the freebase were found that exhibit sufficient stability and solubility properties for incorporation into a pharmaceutical dosage form.

Then, laboratory scale reaction conditions were developed to allow the formation and isolation of salts prepared by reacting the freebase Compound J with 1.05-1.20 equivalents of various acids. Although the specific conditions (e.g., solvents, reaction temperatures, cooling cycles, filtering) necessary to produce each of them differed, 12 potentially useful crystalline salts were identified: hydrochloride, hydrobromide, mesylate, citrate, fumarate, malate, phosphate, sulfate, L-tartrate, ethane-1,2-disulfonate, (+)-(1S)-camsylate, and R-(−)-mandelate. Any crystalline material that was obtained was characterized by XRPD, DSC, and TGA. Stoichiometric ratios were determined by HPCL. Of these, six possible lead candidates were identified:

TABLE 1

| Salt | Molar ratio (acid/base) | Endotherm (° C. onset) |
|---|---|---|
| Phosphate | 1/1 | 182.4 |
| Hemi-citrate | 1/2 | 160.4 |
| L-tartrate | 1/1 | 189.9 |
| Hydrochloride | 1/1 | 245.1, 251.0 |
| Hydrobromide | 1/1 | 254.9 |
| Malate | 1/1 | 165.1 |

Extensive further characterization coupled with the development of large-scale manufacturing, isolation, and purification processes led to the discovery that of all of the salts tested, ((S)-1-((2',6-bis(difluoromethyl)-[2,4'-bipyridin]-5-yl)oxy)-2,4-dimethylpentan-2-aminium dihydrogen phosphate (Compound K) is the most desirable:

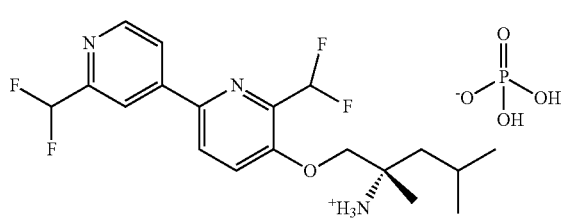

Further study led to the selection of a particular crystalline form of this salt for use in the large-scale manufacture of dosage forms. Referred to herein as Form I, this crystalline form has an XRPD spectrum substantially the same as that shown in FIG. 1, with diffraction peaks at one or more of about 4.81, 5.99, 7.44, 7.89, 11.66, 14.85, 15.77, 19.19, 20.86, 21.65, 23.96, 24.48, or 24.73 degrees 2-theta. When used herein to refer to XPRD peaks, the term "about" means±0.2 degrees 2-theta.

Crystalline Form I of Compound K has a melting point of about 184° C. (see FIG. 2) as determined by differential scanning calorimetry (DSC) (melting endotherm). When referring to a temperature, the terms "substantially" and "about" mean±2° C.

Crystalline Form I of Compound K is the most stable of the forms discovered for this salt: neither the form itself, its morphology, nor its purity changed after having been stored at 40° C. and 75% relative humidity for up to four weeks. Moreover, while Form I has a lower melting point than a hydrochloride salt of Compound J (a form of which was found to have a melting point of about 247° C.), the phosphate salt does not show evidence of concomitant degradation. Instead, the melting of Form I is observed to recrystallize to another, metastable form having a melting point of about 172.5° C. The large-scale manufacture and purification of Form I are further aided by its water solubility, which is 26.8 mg/mL at 25° C. By comparison, a hydrochloride salt of Compound J had a measured aqueous solubility of 2.9 mg/mL at 25° C.

Despite its poor solubility, crystalline forms of the hydrochloride salt of Compound J were prepared. One was discovered with a melting point (decomposition) of about 247° C. An XRPD spectrum of that form exhibited peaks at about 9.2, 11.7, 13.9, 18.7, 22.2, 25.0, and 26.8 degrees 2 theta.

Crystalline Form I of Compound K can be prepared from the freebase (S)-1-((2',6-bis(difluoromethyl)-[2,4'-bipyridin]-5-yl)oxy)-2,4-dimethylpentan-2-amine (Compound J), which itself can be prepared by methods known in the art. See, e.g., U.S. Pat. No. 9,902,722.

In a very general sense, Compound K can be prepared as shown below:

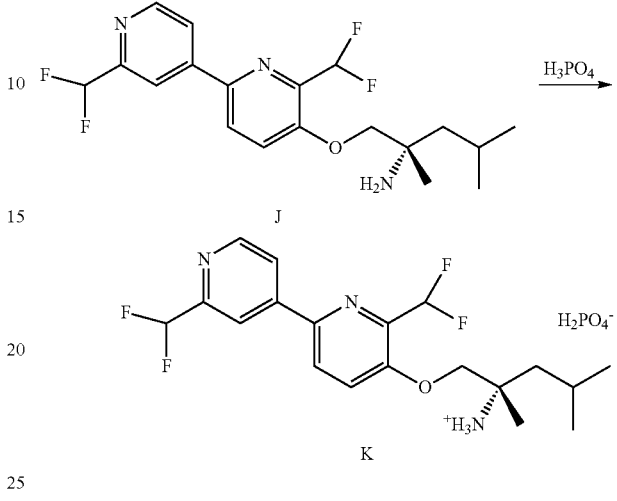

In this approach, Compound K is prepared by contacting Compound J with phosphoric acid in a solvent under conditions sufficient to form Compound K. Examples of solvents include water, methanol, ethanol, n-butanol, isobutanol, t-butanol, methyl t-butyl ether, ethyl acetate, isopropyl acetate, THF and 2-methyl THF, and mixtures thereof. A particular solvent is isopropanol.

In some embodiments of this invention, Compound J is contacted with phosphoric acid at a temperature of from about 0° C. to about 100° C. or from about 50° C. to about 60° C. (When referring to reaction conditions, the term "about" when used to refer to temperature may be construed as ±10° C. unless otherwise indicated.) In some embodiments, Compound J is contacted with phosphoric acid for about 0.5 hours to about 24 hours or for about 2 hours to about 16 hours. (When referring to reaction conditions, the term "about" when referring to time may be construed as ±5 percent unless otherwise indicated. For example, "about 2 hours" is the same as 2 hours±6 minutes.) In some embodiments, from about 0.8 to about 1.2 molar equivalents (e.g., about 1 molar equivalent) of the phosphoric acid is utilized relative to Compound J. (Unless otherwise indicated, the term "about" when referring to molar equivalents or concentration may be construed as ±5 percent.) In some embodiments, the concentration of Compound J in the solvent is from about 2% to about 25%.

In another approach, Compound K is prepared from Compound S as shown below:

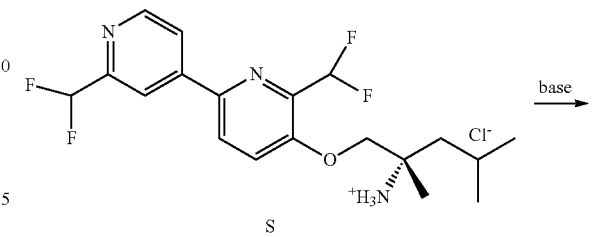

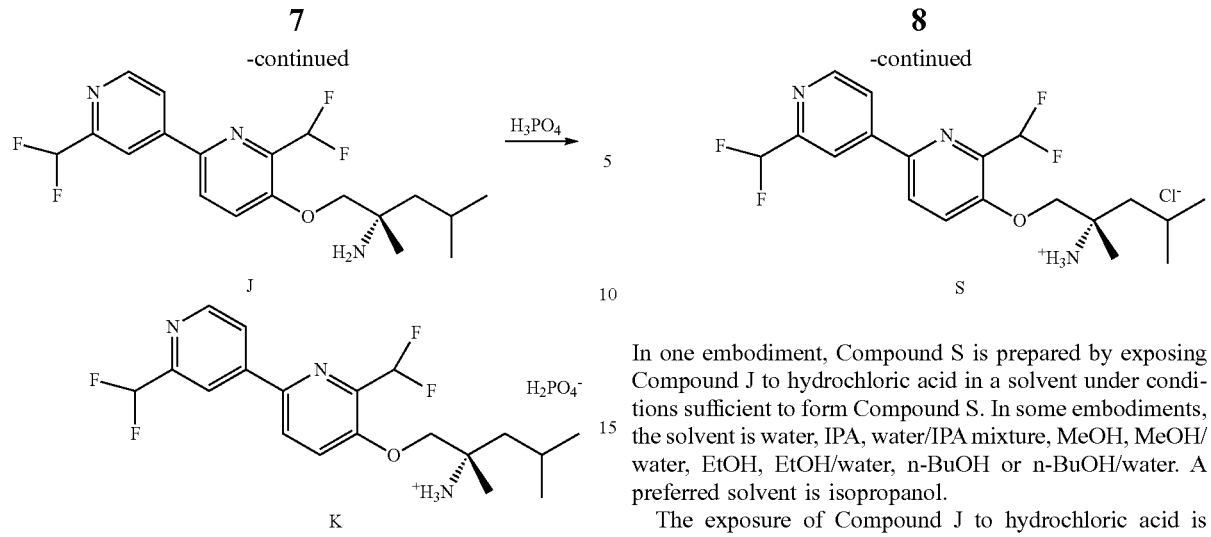

Here, Compound S is neutralized with a base under conditions sufficient to form Compound J, which is contacted with phosphoric acid under conditions sufficient to form Compound K. Suitable bases for the neutralization include NaOH, KOH, $Na_2CO_3$, and $K_2CO_3$. A preferred base is sodium hydroxide.

The neutralization of Compound S with a base may be carried out in a solvent such as water, water/MTBE, water/THF and water/2-MeTHF (a preferred solvent is water/MTBE), and at a temperature of from about 0° C. to about 60° C. (e.g., from about 20° C. to about 40° C.). In some embodiments of the invention, the neutralization is carried out for about 0.5 hours to about 24 hours (e.g., for about 1 hour to about 2 hours.) In some embodiments, from about 0.8 to about 5 molar equivalents of the base is utilized relative to Compound S. In some embodiments, the concentration of Compound S in the solvent is from about 2% to about 25%.

The exposure of Compound J to phosphoric acid in the second step shown above is typically carried out in a solvent such as water, methanol, ethanol, n-butanol, isopropanol, isobutanol, t-butanol, methyl t-butyl ether, ethyl acetate, isopropyl acetate, THF and 2-methyl THF, or mixtures thereof. A preferred solvent is isopropanol.

In some embodiments, the exposure of Compound J to phosphoric acid is carried out at a temperature of from about 0° C. to about 100° C. (e.g., from about 50° C. to about 60° C.) In some embodiments, the exposure of Compound J to phosphoric acid is carried out for about 0.5 hours to about 24 hours (e.g., about seven hours to about 14 hours.) In some embodiments, from about 0.8 to about 1.2 molar equivalents of the phosphoric acid is utilized relative to Compound J in step 2. In some embodiments, the concentration of Compound J in the solvent is from about 2% to about 25%.

Compound S can be prepared as shown below:

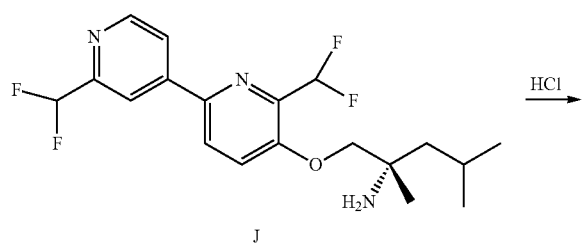

In one embodiment, Compound S is prepared by exposing Compound J to hydrochloric acid in a solvent under conditions sufficient to form Compound S. In some embodiments, the solvent is water, IPA, water/IPA mixture, MeOH, MeOH/water, EtOH, EtOH/water, n-BuOH or n-BuOH/water. A preferred solvent is isopropanol.

The exposure of Compound J to hydrochloric acid is carried out at a temperature of from about 0° C. to about 60° C. (e.g., from about 50° C. to about 60° C.) for about 0.5 hours to about 24 hours (e.g., about 4 hours to about 8 hours.) From about 0.8 to about 1.2 molar equivalents of the hydrochloric acid is typically used relative to Compound J. In some embodiments, the concentration of Compound J in the solvent is from about 2% to about 25%.

5.3 Methods of Use

One embodiment of this invention encompasses methods of inhibiting adaptor associated kinase 1 (AAK1), both in vitro and in vivo, which comprise contacting AAK1 with a compound of the invention.

Another embodiment encompasses methods of treating and managing diseases and disorders mediated by AAK1 activity. Diseases and disorders mediated by AAK1 activity are diseases and disorders that have at least one symptom, the severity or manifestation of which is affected by AAK1 activity. Examples of such diseases and disorders are believed to include Alzheimer's disease, bipolar disorder, pain, Parkinson's disease, schizophrenia (including cognitive deficits in schizophrenia), and viral infection. Particular methods comprise administering to a patient (a human or other mammal) in need thereof a therapeutically or prophylactically effective amount of an AAK1 inhibitor (e.g., a compound disclosed herein).

Another embodiment of this invention encompasses a method of treating or managing a disease or disorder, which comprises administering to a patient in need thereof a therapeutically or prophylactically effective amount of an AAK1 inhibitor, wherein the disease or disorder is Alzheimer's disease, bipolar disorder, pain, Parkinson's disease, schizophrenia (including cognitive deficits in schizophrenia), or viral infection. Particular types of pain include chronic pain, acute pain, and neuropathic pain. Particular types of neuropathic pain include fibromyalgia and peripheral neuropathy (e.g., diabetic neuropathy).

This invention is directed, in part, to methods of combating (e.g., treating) a coronavirus infection. Coronaviruses are a group of related viruses that cause diseases in mammals and birds. In humans, coronaviruses cause respiratory tract infections that can range from mild to lethal. Mild illnesses include some cases of the common cold (which has other possible causes, predominantly rhinoviruses), while more lethal varieties can cause severe acute respiratory syndrome (SARS), Middle East respiratory syndrome (MERS), and coronavirus disease 2019 (COVID-19).

Particular embodiments of the invention comprise treating a patient infected with SARS-CoV2, HCoV NL63, MERS-CoV, CoV-229E, CoV-HKU1, or with a virus sharing at least 95% sequence homology with SARS-CoV2, HCoV NL63, MERS-CoV, CoV-229E, or CoV-HKU1. See, e.g., International Application No. PCT/US21/27946 filed Apr. 19, 2021.

When used to treat or manage a disease or disorder, compounds of the invention are preferably administered as part of a pharmaceutical composition comprising one or more pharmaceutically acceptable carriers, diluents, or excipients.

Pharmaceutical compositions, or formulations, may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

Compounds of the invention may be administered in combination with one or more additional therapeutic or prophylactic agents. For example, when used for the treatment of pain, possible additional agents include immunosuppressive and anti-inflammatory agents.

Immunosuppressants suitable for use in the methods and compositions of this invention include those known in the art. Examples include aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. A particular immunosuppressant is methotrexate.

Additional examples include anti-TNF antibodies, such as adalimumab, certolizumab pegol, etanercept, and infliximab. Others include interleukin-1 blockers, such as anakinra. Others include anti-B cell (CD20) antibodies, such as rituximab. Others include T cell activation blockers, such as abatacept.

Additional examples include inosine monophosphate dehydrogenase inhibitors, such as mycophenolate mofetil (CellCept®) and mycophenolic acid (Myfortic®).

Anti-inflammatory drugs suitable for use in the methods and compositions of this invention include those known in the art. Examples include glucocorticoids and NSAIDs.

Examples of glucocorticoids include aldosterone, beclometasone, betamethasone, cortisone, deoxycorticosterone, dexamethasone, fludrocortisones, hydrocortisone, methylprednisolone, prednisolone, prednisone, triamcinolone, and pharmaceutically acceptable salts thereof.

Examples of NSAID include salicylates (e.g., aspirin, amoxiprin, benorilate, choline magnesium salicylate, diflunisal, faislamine, methyl salicylate, magnesium salicylate, salicyl salicylate, and pharmaceutically acceptable salts thereof), arylalkanoic acids (e.g., diclofenac, aceclofenac, acemetacin, bromfenac, etodolac, indometacin, nabumetone, sulindac, tolmetin, and pharmaceutically acceptable salts thereof), arylpropionic acids (e.g., ibuprofen, carprofen, fenbufen, fenoprofen, flurbiprofen, ketoprofen, ketorolac, loxoprofen, naproxen, oxaprozin, tiaprofenic acid, suprofen, and pharmaceutically acceptable salts thereof), arylanthranilic acids (e.g., meclofenamic acid, mefenamic acid, and pharmaceutically acceptable salts thereof), pyrazolidine derivatives (e.g., azapropazone, metamizole, oxyphenbutazone, phenylbutazone, sulfinprazone, and pharmaceutically acceptable salts thereof), oxicams (e.g., lornoxicam, meloxicam, piroxicam, tenoxicam, and pharmaceutically acceptable salts thereof), COX-2 inhibitors (e.g., celecoxib, etoricoxib, lumiracoxib, parecoxib, rofecoxib, valdecoxib, and pharmaceutically acceptable salts thereof), and sulphonanilides (e.g., nimesulide and pharmaceutically acceptable salts thereof).

Other agents used in the treatment of pain (including but not limited to neuropathic and inflammatory pain) include agents such as pregabalin, lidocaine, duloxetine, gabapentin, carbamazepine, capsaicin, and other serotonin/norepinephrine/dopamine reuptake inhibitors, and opiates (such as oxycontin, morphine, and codeine).

In the treatment of pain caused by a known disease or condition, such as diabetes, infection (e.g., herpes zoster or HIV infection), or cancer, compounds of the invention may be administered in combination with one or more additional therapeutic or prophylactic agents directed at the underlying disease or condition. For example, when used to treat diabetic neuropathy, compounds of the invention may be administered in combination with one or more anti-diabetic agents, anti-hyperglycemic agents, hypolipidemic/lipid lowering agents, anti-obesity agents, anti-hypertensive agents and appetite suppressants. Examples of anti-diabetic agents include biguanides (e.g., metformin, phenformin), glucosidase inhibitors (e.g., acarbose, miglitol), insulins (including insulin secretagogues and insulin sensitizers), meglitinides (e.g., repaglinide), sulfonylureas (e.g., glimepiride, glyburide, gliclazide, chlorpropamide, and glipizide), biguanide/glyburide combinations (e.g., Glucovance), thiazolidinediones (e.g., troglitazone, rosiglitazone, and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, dipeptidyl peptidase IV (DPP4) inhibitors, and sodium-glucose co-transporter 2 (SGLT2) inhibitors (e.g., dapagliflozin, canagliflozin, and LX-4211).

5.4 Pharmaceutical Compositions

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free-flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain antioxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Preferred formulations contain highly pure active pharmaceutical ingredient (API). To that end, potential impurities including those shown below in Table 2 were synthesized and characterized by $^1$H NMR and mass spectroscopy.

TABLE 2

| Impurity No. | Compound |
|---|---|
| 1 | 2',6-bis(difluoromethyl)-5-fluoro-2,4'-bipyridine |
| 2 | 5-(tert-butoxy)-2',6-bis(difluoromethyl)-2,4'-bipyridine |
| 3 | (S)-2-((2',6-bis(difluoromethyl)-[2,4'-bipyridin]-5-yl)oxy)-2-phenylacetic acid |
| 4 | (S)-1-((2',6-bis(difluoromethyl)-[2,4'-bipyridin]-5-yl)oxy)-2,4-dimethylpentan-2-amine |

TABLE 2-continued

| Impurity No. | Compound |
|---|---|
| 5 | 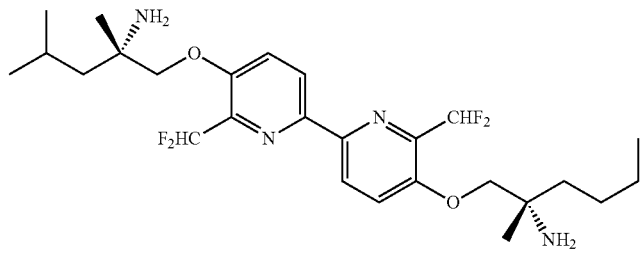<br>(S)-1-((5'-(((S)-2-amino-2,4-dimethylpentyl)oxy)-6,6'-bis(difluoromethyl)-[2,2'-bipyridin]-5-yl)oxy)-2-methylhexan-2-amine |

The compounds in Table 2 were observed at various stages of the lab-scale development work that led to methods of the invention.

This invention comprises a method of testing the purity of Compound J or a pharmaceutically acceptable salt thereof by testing for the presence of one or more of the compounds listed in Table 1. A preferred method comprises testing for the presence of the one or more compounds using mass spectroscopy and/or HPLC.

5.5 Examples

Various embodiments of the invention may be understood by considering the examples provided below. In these examples, unless otherwise indicated, all temperatures are set forth in degrees Celsius and all parts and percentages are by weight. Reagents may be purchased from commercial suppliers and were used without further purification unless otherwise indicated. (Reagents may also be prepared following standard literature procedures known to those skilled in the art.)

Unless otherwise specified, reactions were run at ambient temperature (or room temperature.) Reactions were typically assayed by HPLC and terminated as judged by the consumption of starting material.

Compound structures and purities were confirmed by one or more of the following methods: proton nuclear magnetic resonance ($^1$H NMR) spectroscopy, $^{13}$C NMR spectroscopy, mass spectroscopy, infrared spectroscopy, melting point, X-ray crystallography, LC-MS and/or HPLC. Chemical shifts are reported in parts per million (ppm, δ) downfield from a standard, e.g., an internal standard, such as TMS. Alternatively, $^1$H NMR chemical shifts were referenced to signals from residual protons in deuterated solvents as known in the art. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data were obtained using a mass spectrometer with APCI or ESI ionization.

5.5.1 Synthesis of 6-bromo-2-(dimethoxymethyl)-3-fluoropyridine (Compound L1)

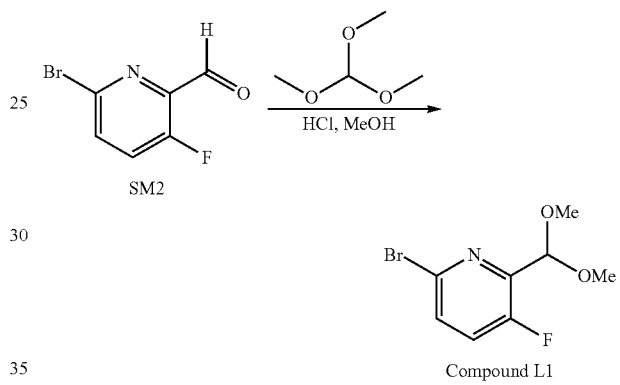

Compound L1

A solution of HCl/MeOH (10 mL of 3.9 M solution, 0.05 eq.) was charged into a mixture of SM2 (158.5 g, 777 mmol, 1 eq.), MeOH (1585 mL, 10V) and trimethoxymethane (166 g, 15.6 mol, 2.0 eq.). The resulting mixture was aged at 60-65° C. (reflux) until reaction completions (3-6 h) and then cooled to 10-20° C. After being concentrated to 2-3V below 50° C. and diluted with 2-Me-THF (10V), the reaction was quenched with 10% K$_2$CO$_3$ (3V). The organic layer was separated and concentrated to 1-2V below 50° C. It was flushed with 2-Me-THF (5V) and then diluted with more 2-Me-THF (5V) to give a solution of Compound L1 in 2-Me-THF (845.2 g, 99% purity, 21.7% assay, 94.4% solution yield). LC-MS: m/z 250, 252, 220, 218 (M-OMe) $^1$H NMR (400 MHz, CHLOROFORM-d) δ 7.38 (dd, J=3.5, 8.6 Hz, 1H), 7.17-7.30 (m, 1H), 5.37-5.48 (m, 1H), 3.39 (s, 6H).

5.5.2 Synthesis of 4-chloro-2-(dimethoxymethyl)pyridine (Compound L2)

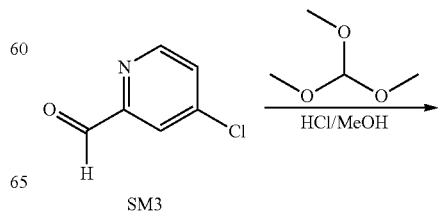

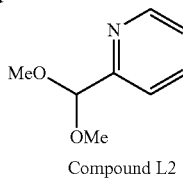

Compound L2

HCl/MeOH (42.3 mL 3.9 M solution, 0.20 eq.) was charged into a mixture of SM3 (117.3 g, 819.5 mmol, 1 eq.), MeOH (1160 mL, 10V) and trimethoxymethane (174 g, 1.64 mol, 2.0 eq.). The mixture was heated to 60-65° C. (reflux) until reaction completion (6-10 h) and then cooled to 10-20° C. After being concentrated to 3-5V and diluted with 2-Me-THF (10V), the reaction was quenched with 10% K₂CO₃ (3V, pH 8-9). The organic layer was separated and concentrated to 1-2V, flushed with 2-Me-THF (5V×2), and then diluted with 2-Me-THF (5V) to give a solution of Compound L2 in 2-Me-THF (588.5 g, 99.18% purity by HPLC, 22.3% assay, 85.3% solution yield). ¹H NMR (400 MHz, CHLOROFORM-d) δ 8.42-8.57 (m, 1H), 7.56 (d, J=2.0 Hz, 1H), 7.25 (dd, J=2.1, 5.3 Hz, 1H), 5.28-5.39 (m, 1H), 3.38 (s, 6H). LC-MS m/z 187, 156 (M-OMe).

5.5.3 Synthesis of 2',6-bis(dimethoxymethyl)-5-fluoro-2,4'-bipyridine phosphate (Compound L4-phosphate)

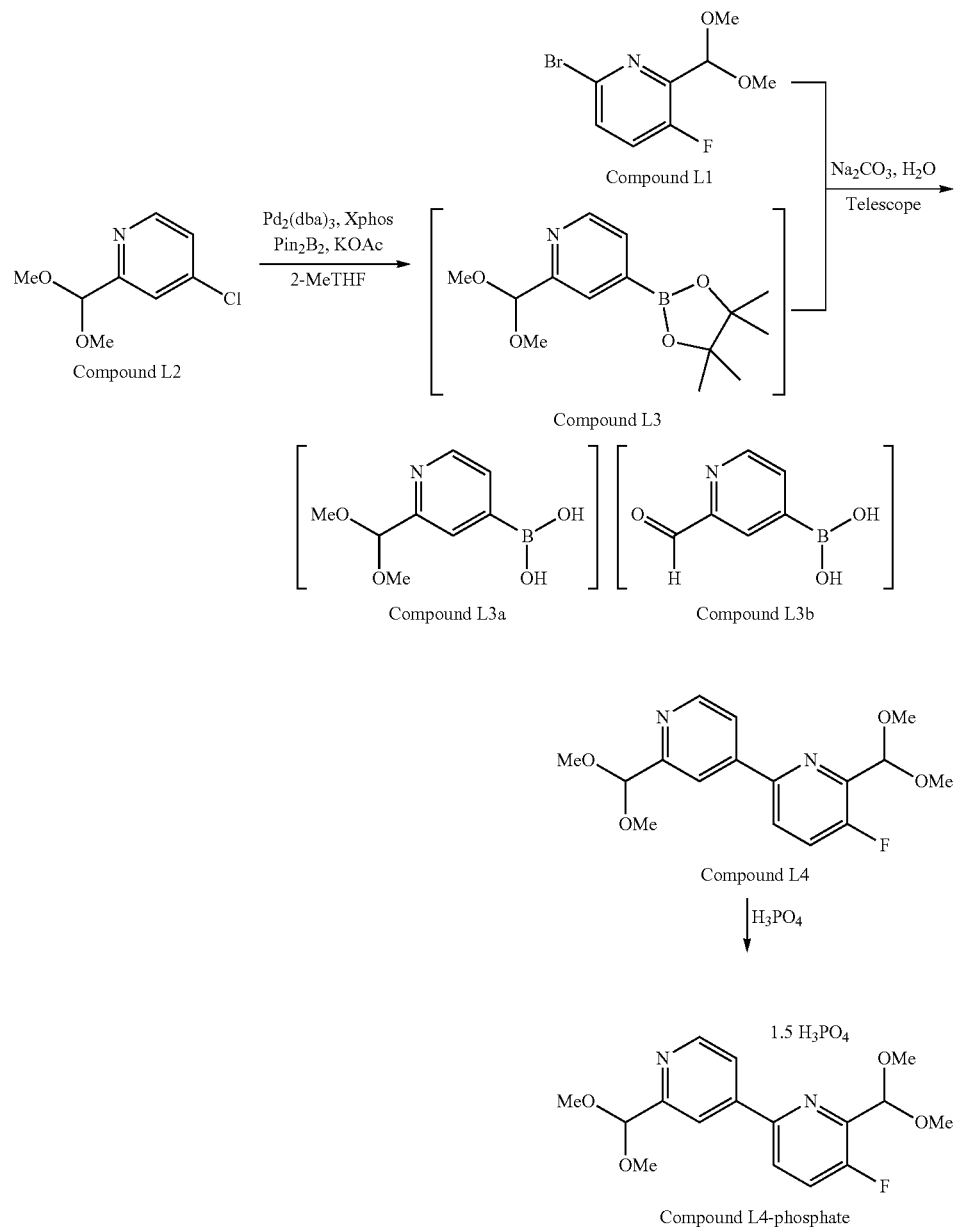

Preparation of L3: A mixture of compound L2 in 2-Me-THF (95.5 g, 1.00 eq., 5-6V), 2-Me-THF (10V), Pin$_2$B2 (1.05 eq.), KOAc (3.0 eq.) and Xphos (0.02 eq.) was degassed by sparging with N$_2$. Pd$_2$(dba)$_3$ (0.01 eq.) was added, and the mixture degassed by sparging with N$_2$ again. The reaction mixture was heated to 70-80° C. and stirred until the borylation of L2 was complete (16-24 h) to give L3, which was used directly for the next Suzuki coupling step.

Preparation of L4 via Suzuki coupling of L3 and L1: After cooling to 15-25° C., a solution of compound L1 in 2-Me-THF (0.96 eq., 5-6V), Na$_2$CO$_3$ (2.0 eq. solid) and H$_2$O (5V) were added sequentially. After degassing by sparging with N$_2$, the reaction mixture was aged at 70-80° C. until the Suzuki coupling was complete (16-24 h). After cooling to 15-25° C., the reaction mixture was filtered through a pad of diatomite (0.5×) and the filter-cake was rinsed with 2-Me-THF (1-2V). The organic layer in the filtrate was separated, concentrated to 1-2V, diluted with toluene (10V) and washed with L-cysteine/NaOH (pH>10)(5λ, ratio of L-cysteine/NaOH/H$_2$O: 1/0.5/9) twice. The organic layer was then washed with H$_2$O (5λ) and concentrated to 5V to give a toluene solution of Compound L4 free base in toluene. An analytical sample of L4 free base was obtained by crystallization in heptane/MTBE. $^1$H NMR (400 MHz, chloroform-d) δ 8.66-8.77 (m, 1H), 8.06 (d, J=1.22 Hz, 1H), 7.94 (dd, J=1.77, 5.20 Hz, 1H), 7.86 (dd, J=3.55, 8.56 Hz, 1H), 7.51-7.60 (m, 1H), 5.63 (s, 1H), 5.44-5.48 (m, 1H), 3.54-3.60 (m, 6H), 3.43-3.49 (m, 6H); mp 41.8° C. (DSC peak); XRPD 2θ: 6.70, 7.61, 9.67, 13.56, 13.77, 13.99, 15.36, 19.36, 20.71, 21.81, 23.10, 26.96, 27.72, 28.02, 29.36, 31.88, 32.04, 39.09.

Preparation of L4 phosphate: A solution of 85% H$_3$PO$_4$ (1.6 eq. based on Compound L4 free base) in MeOH (1-2V) was added over 2 h to the above L4 solution in toluene to afford a suspension. The suspension was concentrated to 3V below 45° C. and n-heptane (10V) was added over 2 h. The mixture was concentrated to 10V below 45° C. and the batch temperature was adjusted to 15-25° C. After stirring for 6-8 h, the mixture was filtered, and the filter-cake rinsed with n-heptane (1-2V). The wet cake was dried with a slight N$_2$ sweep under reduced pressure at 40° C. to give 190.5 g of L4-Phosphate (93.2% yield). $^1$H NMR (400 MHz, DMSO-d$_6$) δ 8.63-8.72 (m, 1H), 8.24 (dd, J=3.6, 8.7 Hz, 1H), 8.11 (d, J=1.1 Hz, 1H), 8.01 (dd, J=1.8, 5.2 Hz, 1H), 7.92 (dd, J=8.7, 9.9 Hz, 1H), 5.58 (s, 1H), 5.36 (s, 1H), 3.43 (s, 6H), 3.35 (s, 6H). LC-MS: [M+H]$^+$323.2; mp. 124.2° C. (DSC peak); XRPD 2θ: 4.87, 7.35, 9.20, 12.76, 14.66, 15.06, 15.92, 16.99, 19.56, 19.81, 20.26, 21.55, 22.12, 23.09, 23.39, 23.73, 25.61, 26.25, 27.48, 27.73, 28.26, 29.55, 30.35, 31.10, 31.82, 34.13, 34.68, 36.04, 39.48.

5.5.4 Synthesis of 5-fluoro-[2,4'-bipyridine]-2',6-dicarbaldehyde (Compound Q)

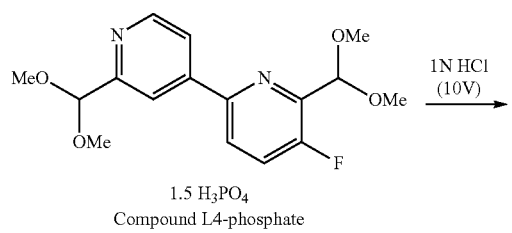

Compound L4-phosphate

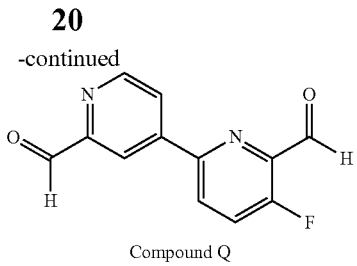

Compound Q

A mixture of compound L4-Phosphate (177 g, 111 g L4 free base=1.0×), 1N HCl (1110 mL, 10V) and toluene (555 mL, 5V) was stirred at 15-25° C. for 0.5-1.0 h. The organic phase was separated off and the aqueous layer was stirred at 55-60° C. for 2 h. The mixture was slowly (3 h) concentrated to remove generated MeOH under reduced pressure (−0.08 to −0.085 Mpa) at 55-60° C. and then cooled to 30-40° C. DCM (777V) was charged and the pH of the mixture was adjusted to 5-7 with 15% Na$_2$CO$_3$ (3.5-4.5×). The layers were separated, and the aqueous layer was extracted with DCM (2V). The combined organic layer was washed with H$_2$O (5V) and filtered through a pad of Na$_2$SO$_4$ (1×). The filter-pad was rinsed with DCM (2V) and the combined filtrate concentrated to 8-10V. The reactor wall was spray washed with 2V DCM and then n-heptane (8-10V) was charged over 2.0-5.0 h. The mixture was concentrated to 10-12V below 60° C. under normal atmospheric pressure (residual DCM in supernatant ≤40%). The suspension was aged at 30-40° C. for 1.0-2.0 h, 5-10° C. for 6-8 h and filtered. The filter-cake was washed with 1:4 DCM/n-heptane (1-2V) and dried under reduced pressure at 40-50° C. to give 80.19 g Compound Q (98% yield). LC-MS: [M+H]$^+$ 231; [M+H+H$_2$O]$^+$249; $^1$H NMR (400 MHz, CHLOROFORM-d) δ 10.27 (s, 1H), 10.18 (s, 1H), 8.91-9.00 (m, 1H), 8.51-8.59 (m, 1H), 8.24-8.31 (m, 1H), 8.17 (dd, J=3.5, 8.7 Hz, 1H), 7.77 (t, J=9.0 Hz, 1H); mp. 150° C. (DSC peak).

5.5.5 Synthesis of 2',6-bis(difluoromethyl)-5-fluoro-2,4'-bipyridine (Compound H)

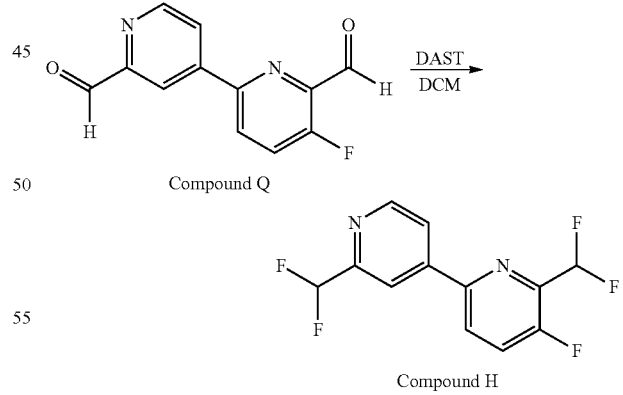

A solution of compound Q (30.0 g, 1.00×) and Et$_3$N (0.044×) in dry DCM (KF≤0.02%, 20×) was cooled to 0-5° C. DAST (3.50×) was slowly added at 0-10° C. and the mixture was then aged at 20-25° C. until reaction completion (~24 h). The reaction mixture was quenched into 15% K$_2$CO$_3$ (28×) at 0-20° C. for two hours and aged at 20-25° C. for 0.5 h. The organic layer was separated, cooled to 10-20° C. and treated with 1 M HCl (9.9-11.1×) at 10-25° C.

for 0.5-1 h. After settling for 0.5 h, the mixture was filtered through a pad of Diatomite earth (~0.5×) followed by a small rinse DCM (2.0-3.0×). The filtrate was settled, and the organic layer was separated, washed with H₂O (10×) and filtered through a pad of silica gel (~1.5×). The silica pad was washed with DCM (5.0×-6.0× three times) until the purity of Compound H in the filtrate fraction decreased <90%. The combined filtrate was concentrated to ~2-3V below 30° C. and then co-distilled with isopropanol 50° C. until residual DCM <5.0% (6-7× total IPA used) with a final volume of 3-4V. The distillation residue was aged at 55-60° C. for 0.5 h, cooled to 35-40° C., aged for 0.5 h. Water (9.0-10.0×) was slowly added at 33-40° C. (1-3 h) and the mixture stirred for 0.5 h. After aging at 15-20° C., the suspension was filtered and the filter-cake washed sequentially with IPA/H₂O (1:4, w/w, 1×), H₂O (2×). The wet-cake was dried under reduced pressure at 40-45° C. until KF<0.3% and residual IPA <0.1% (18-24 h) to give 30.15 g compound H (82% yield). Melting point (mp) 75° C. (DSC peak). LC-MS: [M+H]⁺ 275.2; ¹H NMR (400 MHz, CHLOROFORM-d) δ 8.71-8.89 (m, 1H), 8.22 (s, 1H), 7.91-8.12 (m, 2H), 7.71 (t, J=8.9 Hz, 1H), 7.00 (s, 1H), 6.87 (s, 1H), 6.82-7.05 (m, 1H), 6.59 (s, 1H), 6.73 (s, 1H).

5.5.6 Synthesis of (S)-2-amino-2,4-dimethylpentan-1-ol benzoate (Compound D-Benzoate)

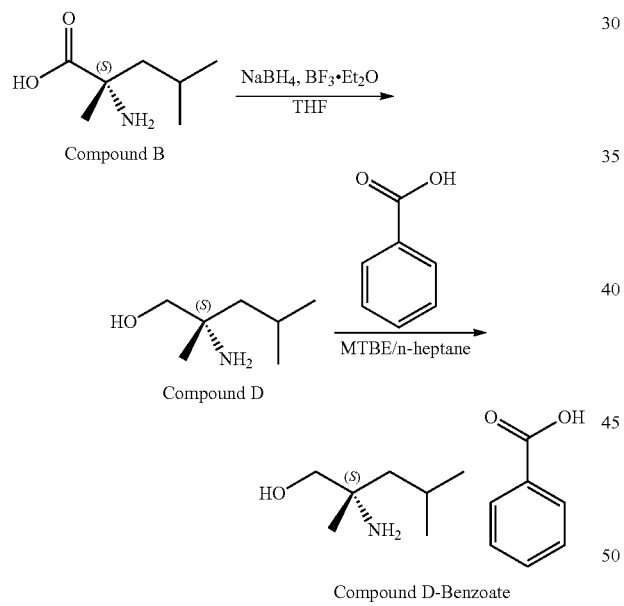

BF₃·Et₂O (200 g, 2.0 equiv) was slowly added to a mixture of NaBH₄ (53 g, 2.0 equiv) in THF (1.0 L) at 0-10° C. The reaction mixture was warmed to 15 C and then (S)-(α)methylleucine (100 g, 1.0 equiv) was added over 1 h at <25° C. The mixture was aged at 20-25° C. for 5-8 hours and slowly quenched into 10% aq. NaOH (750 mL) at 25-30° C. The organic layer was separated, washed with 15% aq. NaCl (200 mL) and then diluted with n-heptane (300 mL). 2N HCl (~300 mL) was added to the mixture until the pH reached 1-2. The organic layer was separated and extracted with 1 N HCl (300 mL). The combined aqueous layer was basified with 30% NaOH (~500 mL) until pH>13 and then extracted with MTBE (500 mL×3). The combined organic extract was dried over anhydrous Na₂SO₄ (100-200 g), filtered, concentrated to ~200 mL, and then flushed with MTBE (200-500 mL) until moisture content in the concentrate was <0.5%. The solution of the amino alcohol D was then slowly (5 h) added to a solution of benzoic acid (93 g, 1.1 equiv) in MTBE (500 mL) at 45-50° C. After stirring for 1 h, the mixture was slowly (5-8 h) cooled to 20-25° C. and aged for 5-8 h to give a suspension. The suspension was filtered, the filter-cake washed with 1/1 MTBE/n-heptane (150 mL) and dried at 40-50° C. under reduced pressure to give Compound D-benzoate in 92% yield. mp. 125.4° C. (DSC peak); ¹H NMR (400 MHz, METHANOL-d₄) δ 7.88-7.99 (m, 2H), 7.27-7.46 (m, 3H), 3.45-3.62 (m, 2H), 1.69-1.87 (m, 1H), 1.56-1.66 (m, 1H), 1.44-1.54 (m, 1H), 1.29 (s, 3H), 1.00 (d, J=6.60 Hz, 6H); XRPD 2θ: 6.67, 6.83, 12.84, 13.37, 15.16, 16.95, 17.83, 19.90, 20.32, 21.23, 22.28, 23.70, 24.09, 24.42, 26.24, 26.91, 27.49, 30.60, 32.64, 33.98, 34.98, 35.13.

5.5.7 Synthesis of (S)-1-((2',6-bis(difluoromethyl)-[2,4'-bipyridin]-5-yl)oxy)-2,4-dimethylpentan-2-amine hydrochloride (Compound S)

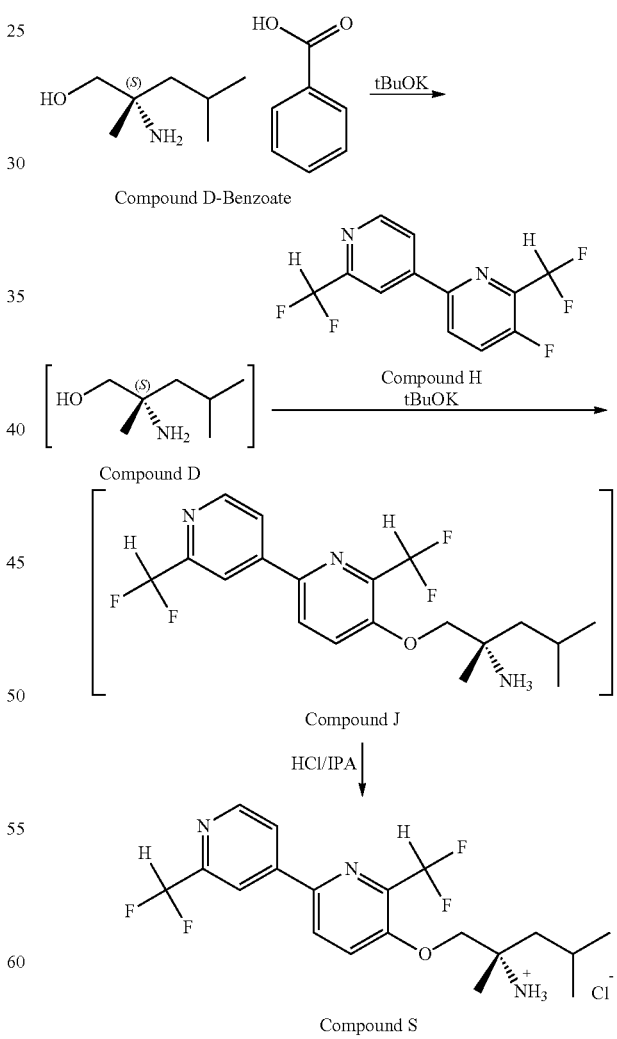

Solid t-BuOK (2.5-3.0 eq. based on Compound H) was charged in portions to a mixture of Compound D-benzoate (1.2 eq. based on Compound H) and THF (10.5-11.6×) at 15-20° C. The mixture was warmed to 20-25° C., stirred for 3-5 h and then cooled to 0-5° C. A solution of compound H (1.00×) in THF (3.6-4.5×) was slowly (~1 h) added while maintaining the batch temperature below 20° C. The reaction mixture was aged at 20-25° C. until reaction completion (1-3 h). MTBE (6×) was added, and the mixture cooled to 10-15° C. H$_2$O (9.0-11.0×) was added slowly (1-3 h) while keeping the batch temperature below 25° C. The layers were separated, and the aqueous layer was extracted with MTBE (2.2×). The combined organic layer was concentrated to 2-3V under reduced at below 30° C. Free base compound J: $^1$H NMR (400 MHz, DMSO-d$_6$) δ 8.70-8.84 (m, 1H), 8.40 (d, J=8.8 Hz, 1H), 8.33 (s, 1H), 8.22 (br d, J=5.0 Hz, 1H), 7.81 (d, J=8.8 Hz, 1H), 7.17-7.41 (m, 1H), 6.89-7.13 (m, 1H), 3.82-3.95 (m, 2H), 1.74-1.88 (m, 1H), 1.55 (br s, 2H), 1.33-1.46 (m, 2H), 1.12 (s, 3H), 0.93 (t, J=7.1 Hz, 6H). After solvent swap to IPA by co-distillation (6.0-6.5×) to 2-3V, more IPA (3.8-4.2×) was added and the mixture was heated to 50-60° C. A solution of 35% HCl (0.44-0.47×) in IPA (1.3-1.5×) was added slowly (~1 h) while keeping the batch at 50-60° C. The resulting suspension was aged at 50-60° C. for 1.0-2.0 h, cooled to 20-30° C. in 2.0-4.0 h, stirred at 20-30° C. for 1.0-2.0 h and then filtered. The filter-cake was washed with MTBE (3.5-4.0×) and dried under reduced pressure at 40-50° C. for 16-24 h to give Compound S. LC-MS m/z 386.1; mp. 246.4° C. (DSC peak), $^1$H NMR (400 MHz, DMSO-d$_6$) δ 8.81 (d, J=5.3 Hz, 1H), 8.51 (br s, 2H), 8.45 (d, J=8.9 Hz, 1H), 8.34 (s, 1H), 8.24 (d, J=5.1 Hz, 1H), 7.91 (d, J=8.9 Hz, 1H), 7.56-7.87 (m, 1H), 6.90-7.23 (m, 1H), 4.29 (s, 2H), 1.72-1.91 (m, 2H), 1.54-1.72 (m, 1H), 1.42 (s, 3H), 0.86-1.00 (m, 6H).

5.5.8 Synthesis of (S)-1-((2',6-bis(difluoromethyl)-[2,4'-bipyridin]-5-yl)oxy)-2,4-dimethylpentan-2-amine phosphate (Compound K)

A mixture of compound S (9.5 kg, 1.0×), MTBE (76.0 kg, 8.0×), water (50.0 kg, 5.3×) was treated with 20% aqueous NaOH (0.95 kg NaOH solid in 4.0 kg water) at 35-40° C. until all solid dissolved (2.0-5.0 h). The reaction mixture was cooled to 20-25° C. and stirred for 1.0-2.0 h. The organic layer was separated, washed with water (46.5 kg, 4.9×) and concentrated to ~25 L (2-3×) at ≤30° C. under reduced pressure. After solvent swap to IPA by co-distillation under reduced pressure ≤50° C. (79.0 kg IPA, 8.3×) with a final volume of 29-38 L (3-4×), the distillation residue was diluted with IPA (60 kg) and heated to 50-60° C. A solution of H$_3$PO$_4$ (2.8 kg, 0.29×) in IPA (5.0 kg, 0.53×) was added over 2.0-4.0 h. More IPA (22.0 kg, 2.3×) was added and the batch was stirred for 2.0-4.0 h at 50-60° C. The batch was cooled to 15-20° C. over 2.0-4.0 h and then stirred for 1.0-2.0 h at 15-20° C. The resulting suspension was filtered, and the filter cake washed sequentially with IPA (27.0 kg, 2.84×) and MTBE (31 kg, 3.3×). The wet-cake was dried at 45-55° C. for 17-24 h under reduced pressure to give compound K. The salt ratio between Compound J and phosphoric acid in Compound K was determined to be 1:1 (two separate HPLC methods using a UV and an IC detector, respectively). The purity of Compound K was 98.7-99.9 area % by HPLC. The crystallinity of Compound K was confirmed by XRPD and further supported by DSC. $^1$H NMR (400 MHz, DMSO-d$_6$) δ 8.78 (d, J=5.1 Hz, 1H), 8.41 (d, J=8.8 Hz, 1H), 8.31 (s, 1H), 8.21 (d, J=5.1 Hz, 1H), 7.88 (brd, H), 7.47 (t, J$_{H-C-F}$=54 Hz, 1H), 7.04 (t, J$_{H-C-F}$=54 Hz, 1H), 4.03-4.29 (m, 2H), 1.72-1.87 (m, 1H), 1.60-1.69 (m, 1H), 1.49-1.59 (m, 1H), 1.33 (s, 3H), 0.92 (d, J=6.6, 3H), 0.87 (d, J=6.6, 3H); $^{13}$C NMR (100 MHz, DMSO-d$_6$) δ 21.62, 22.74, 24.61, 24.82, 44.69 54.57, 72.80, 110.53 (t, J$_{C-F}$=237 Hz), 113.84 (t, J$_{C-F}$=238 Hz), 116.68, 122.19, 125.03, 140.07 (t, J$_{C-F}$=22 Hz), 144.13, 145.98, 150.52, 152.80 (t, J$_{C-F}$=25 Hz), 153.51. XRPD: 4.80, 5.99, 7.43, 7.88, 9.57, 11.58, 14.84, 15.21, 15.75, 17.91, 18.83, 19.17, 20.41, 20.84, 21.67, 23.23, 23.95, 24.41, 24.72, 25.27, 26.37, 30.14.

5.5.9 Synthesis of (S)-1-((2',6-bis(difluoromethyl)-[2,4'-bipyridin]-5-yl)oxy)-2,4-dimethylpentan-2-amine phosphate (Compound K)

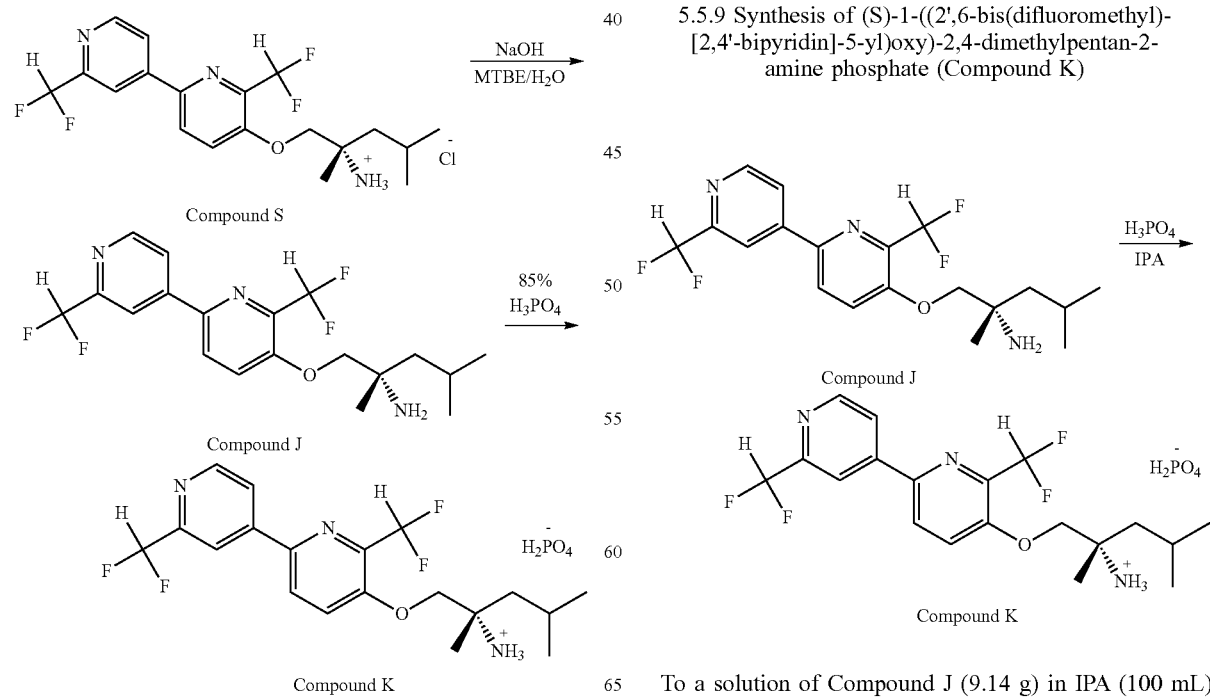

To a solution of Compound J (9.14 g) in IPA (100 mL) was added Compound K seed (0.18 g) at 50-60° C. A solution of 85% phosphoric acid (2.87 g, 1.05 equiv) in IPA (7 mL) was added over a period of 2-4 h. The suspension was aged for 2-4 h, cooled to 15-20° C. over 2-4 h and aged for 1-2 h. The suspension was filtered, and the filter cake washed with IPA (20 mL) followed by MTBE (44 mL). The wet cake was dried under reduced pressure at 45-55° C. for 17-24 h to give 11.3 g of Compound K, 98% yield.

Compound K seed formation: IPA (1.0 mL) was added to Compound J (50.08 mg, 0134 mmol, 1.0 eq.) to form a clear solution at ambient temperature and then phosphoric acid (0.156 mL, 1M in IPA, 0.156 mmol, 1.20 eq.) was added. The mixture was stirred for 6 h to give a suspension and then aged at 60° C. for 30 min. After cooling to room temperature, heptane (0.5 mL) was added, and the resulting mixture stirred for 1 h. The resulting suspension was filtered, and the filter-cake was washed with MTBE (0.5 mL), dried at 45-48° C. under reduced pressure overnight to afford Compound K seed (59.28 mg, 94.4% yield).

The salt ratio, purity, XRPD, DSC and TGA data are substantially identical to the data obtained for Compound K in Example 2.

5.5.10 Tablet Dosage Forms

Tablets comprising 10, 20, or 50 mg of Compound K were prepared in a batch of 20,000 using the ingredients shown below:

TABLE 3

| | Amount (mg) Per | | |
| --- | --- | --- | --- |
| Ingredient | 10 mg batch | 20 mg batch | 50 mg batch |
| Compound K[1,2] | 252.8 | 505.6 | 1264.0 |
| Silicified Microcrystalline Cellulose | 2758.6 | 2632.2 | 2253.0 |
| Dibasic Calcium Phosphate, Anhydrous | 2758.6 | 2632.2 | 2253.0 |
| Croscarmellose Sodium | 120.0 | 120.0 | 120.0 |
| Talc | 120.0 | 120.0 | 120.0 |
| Colloidal Silicon Dioxide | 30.0 | 30.0 | 30.0 |
| Hydrogenated Vegetable Oil | 160.0 | 160.0 | 160.0 |
| Total (Core Tablet) | 6200.0 | 6200.0 | 6200.0 |
| OpaDry II White[3] | 248.0 | 248.0 | 248.0 |
| Total (Film coated Tablet) | 6448.0 | 6448.0 | 6448.0 |

[1]One mg of Compound K is equivalent to 0.7973 mg of the free base (Compound J).
[2]The quantity of Compound K is adjusted for potency based on the supplier Certificate of Analysis, Assay (Weight %, HPLC). A proportionate quantity of Silicified Microcrystalline Cellulose and Dibasic Calcium Phosphate, Anhydrous is adjusted accordingly.
[3]Opadry II White is dispersed in Purified Water at 15% solids to coat the cores. A 50% overage of the coating is prepared to compensate for losses during film-coating and to guarantee the amount applied per tablet. Purified Water is removed during production.

A flowchart representing the manufacture of the tablets is shown in FIG. 3. The same process is used for all three strengths; however, the compression/coating flow chart only depicts the process for the 50 mg strength. The excipient grade, screen sizes and blend times, as depicted in the flow charts, may be adjusted based on process requirements and batch sizes. Referring to FIG. 3, the following steps were followed to prepare solid oral dosage forms of Compound K:

1. The quantity of Compound K is adjusted for potency based on the supplier Certificate of Analysis, Assay (Weight %, HPLC).
2. Screen Compound K, Silicified Microcrystalline Cellulose, Dibasic Calcium Phosphate, Anhydrous, Croscarmellose Sodium into a bin blender and blend. Note: A proportionate quantity of Silicified Microcrystalline Cellulose and Dibasic Calcium Phosphate, Anhydrous is adjusted according to the Compound K potency, as determined in Step 1.
3. Screen Talc and Colloidal Silicon Dioxide into the blend from Step 2 and blend.
4. Screen Hydrogenated Vegetable Oil into the blend from Step 3 and blend.
5. Compress the blend from Step 4.
6. The tablet cores, from Step 5, are subsequently coated with an aqueous dispersion of Opadry II White for an approximate weight gain of 4%.
7. The coated tablets, from Step 6, are packaged into HDPE bottles induction sealed with a child resistant cap.

Each reference (e.g., patents, patent applications, and publications) cited herein is incorporated herein by reference in its entirety.

What is claimed is:

1. A crystalline compound, which is crystalline(S)-1-((2',6-bis(difluoromethyl)-[2,4'-bipyridin]-5-yl)oxy)-2,4-dimethylpentan-2-aminium dihydrogen phosphate (Compound K):

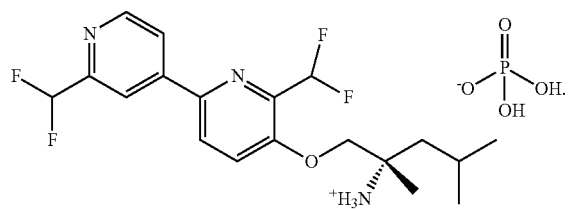

having an XPRD pattern comprising peaks at one or more of about 4.81, 5.99, 7.44, 7.89, 11.66, 14.85, 15.77, 19.19, 20.86, 21.65, 23.96, 24.48, or 24.73 degrees 2-theta.

2. The crystalline compound of claim 1, which has a melting point of about 184° C.

3. A composition comprising an active pharmaceutical ingredient (API), an excipient, and a lubricant, wherein the API is the crystalline compound of claim 1.

4. The composition of claim 3, which comprises less than 0.05 weight percent of at least one of: 2',6-bis(difluoromethyl)-5-fluoro-2,4'-bipyridine; 5-(tert-butoxy)-2',6-bis(difluoromethyl)-5-fluoro-2,4'-bipyridine: (S)-2-((2',6-bis(difluoromethyl)-[2,4'-bipyridin]-5-yl)oxy)-2-phenylacetic acid; (S)-1-((2',6-bis(difluoromethyl)-[2,4'-bipyridin]-5-yl)oxy)-2,4-dimethylpentan-2-amine; or(S)-1-((5'-(((S)-2-amino-2,4-dimethylpentyl)oxy)-6-6'-bis(difluoromethyl)-[2,2'-bipyridin]-5-yl)oxyl)-2-methylhexan-2-amine the compounds listed in Table 2.

5. A tablet comprising the composition of claim 3.

6. The tablet of claim 5, which is coated.

7. The tablet of claim 5, which comprises 10, 20, or 50 mg of the API.

8. A method of treating or managing pain in a patient, which comprises administering to a patient in need thereof a therapeutically effective amount of a compound of claim 1.

9. A method of treating or managing pain in a patient, which comprises administering to a patient in need thereof a therapeutically effective amount of the composition of claim 3.

10. The method of claim 8, wherein the pain is neuropathic pain.

11. The method of claim 9, wherein the pain is neuropathic pain.

\* \* \* \* \*